United States Patent
Govari et al.

(10) Patent No.: US 11,259,751 B2
(45) Date of Patent: Mar. 1, 2022

(54) RECORDING APPARATUS AND METHOD FOR NOISE REDUCTION

(71) Applicant: Biosense Webster (Israel) Ltd., Yokneam (IL)

(72) Inventors: Assaf Govari, Haifa (IL); Vadim Gliner, Haifa (IL); Andres Claudio Altmann, Haifa (IL); Alon Boumendil, Givat Nili (IL)

(73) Assignee: Biosense Webster (Isreal) Ltd., Yokneam (IL)

( * ) Notice: Subject to any disclaimer, the term of this patent is extended or adjusted under 35 U.S.C. 154(b) by 118 days.

(21) Appl. No.: 16/579,359

(22) Filed: Sep. 23, 2019

(65) Prior Publication Data

US 2021/0022684 A1    Jan. 28, 2021

Related U.S. Application Data

(60) Provisional application No. 62/877,218, filed on Jul. 22, 2019.

(51) Int. Cl.
*A61B 5/333* (2021.01)
*A61B 5/00* (2006.01)
*A61B 5/283* (2021.01)

(52) U.S. Cl.
CPC .......... *A61B 5/7203* (2013.01); *A61B 5/283* (2021.01); *A61B 5/333* (2021.01); *A61B 5/6852* (2013.01); *A61B 5/7225* (2013.01); *A61B 5/7257* (2013.01)

(58) Field of Classification Search
None
See application file for complete search history.

(56) References Cited

U.S. PATENT DOCUMENTS

| 4,537,200 | A | * | 8/1985 | Widrow | ................. A61B 5/301 600/509 |
| 5,924,980 | A | * | 7/1999 | Coetzee | ............ G06K 9/00503 600/300 |
| 9,504,522 | B2 | | 11/2016 | Saba et al. | |

(Continued)

FOREIGN PATENT DOCUMENTS

WO    WO 2017/136599 A1    8/2017
WO    WO 2017/210352 A1    12/2017

OTHER PUBLICATIONS

European Search Report dated Dec. 3, 2020, EP Application No. 20 18 6893.

*Primary Examiner* — Kennedy Schaetzle

(57) ABSTRACT

In one embodiment, an electrical activity measurement system includes a catheter to be inserted into a body part and including at least one electrode, signal processing circuitry coupled to receive an intracardiac electrogram (IEGM) signal from the at least one electrode and process the IEGM signal for output to a recording apparatus via a cable, which picks up surrounding electrical noise, and feedback circuitry configured to receive at least some of the electrical noise picked up by the cable, and provide a feedback signal indicative of the received electrical noise to the signal processing circuitry, which is configured to compensate at least partially for the electrical noise, which is not yet in the IEGM signal but will be added to the IEGM signal in the cable, responsively to the feedback signal to produce a noise-compensated IEGM signal for output to the recording apparatus via the cable.

17 Claims, 10 Drawing Sheets

(56) References Cited

U.S. PATENT DOCUMENTS

| | | |
|---|---|---|
| 9,591,981 B2 | 3/2017 | Levin et al. |
| 2002/0133208 A1 | 9/2002 | Connelly |
| 2003/0083713 A1* | 5/2003 | Palreddy .................. A61N 1/37 |
| | | 607/28 |
| 2003/0171661 A1* | 9/2003 | Tong ........................ A61B 5/30 |
| | | 600/300 |
| 2010/0114201 A1 | 5/2010 | Donofrio et al. |
| 2011/0066052 A1* | 3/2011 | Mascarenhas ........... A61B 5/30 |
| | | 600/509 |
| 2013/0027058 A1* | 1/2013 | Dubielczyk .............. G01R 1/18 |
| | | 324/613 |
| 2015/0094561 A1* | 4/2015 | Rey ...................... A61B 5/0205 |
| | | 600/411 |
| 2016/0183876 A1 | 6/2016 | Shah et al. |
| 2017/0112405 A1 | 4/2017 | Sterrett et al. |
| 2018/0303414 A1 | 10/2018 | Toth et al. |

* cited by examiner

RECORDING APPARATUS AND METHOD FOR NOISE REDUCTION

RELATED APPLICATION INFORMATION

The present application claims benefit under 35 USC 119 of U.S. Provisional Patent Application No. 62/877,218, filed on Jul. 22, 2019, which prior patent application is hereby incorporated by reference as if set forth in full herein.

FIELD OF THE INVENTION

The present invention relates to medical equipment, and in particular, but not exclusively to, reducing noise in electrogram signals.

BACKGROUND

Electrical noise can be a significant problem in recording electrophysiological signals.

U.S. Pat. No. 9,591,981 to Levin, et al., describes a method for acquiring electrical signals from a living subject, including injecting, via an injection electrode attached to the subject, a known calibration signal to the subject and measuring respective levels of output signals generated at input electrodes attached to the subject in response to the calibration signal. The method further includes deriving respective weighting factors for the input electrodes in response to the respective levels, and applying the respective weighting factors to physiological signals acquired by the input electrodes, so as to generate respective corrected physiological signals.

US Patent Publication 2010/0114201 of Donofrio, et al., describes electrical crosstalk between two implantable medical devices or two different therapy modules of a common implantable medical device may be evaluated, and, in some examples, mitigated. In some examples, one of the implantable medical devices or therapy modules delivers electrical stimulation to a non-myocardial tissue site or a nonvascular cardiac tissue site, and the other implantable medical device or therapy module delivers cardiac rhythm management therapy to a heart of the patient.

US Patent Publication 2002/0133208 of Connelly describes an electromagnetic immune tissue invasive system includes a primary device housing. The primary device housing having a control circuit therein. A shielding is formed around the primary device housing to shield the primary device housing and any circuits therein from electromagnetic interference. A lead system transmits and receives signals between the primary device housing. The lead system is either a fiber optic system or an electrically shielded electrical lead system.

US Patent Publication 2017/0112405 of Sterrett, et al., describes an integrated electrode structure comprising a catheter shaft comprising a proximal end and a distal end, the catheter shaft defining a catheter shaft longitudinal axis. A flexible tip portion can be located adjacent to the distal end of the catheter shaft, the flexible tip portion comprising a flexible framework. A plurality of microelectrodes can be disposed on the flexible framework and can form a flexible array of microelectrodes adapted to conform to tissue. A plurality of conductive traces can be disposed on the flexible framework, each of the plurality of conductive traces can be electrically coupled with a respective one of the plurality of microelectrodes.

US Patent Publication 2018/0303414 of Landy, et al., describes systems, devices, and methods for performing precise treatment, mapping, and/or testing of tissues, for administering an agent to one or more precise regions within a tissue mass, for treating targeted regions within a tissue mass are disclosed. Systems, devices, and methods for identifying, localizing, monitoring neural traffic in the vicinity of, quantifying neural traffic in the vicinity of, and mapping neural traffic near targeted regions within a tissue mass are disclosed.

SUMMARY

There is provided in accordance with an embodiment of the present disclosure, an electrical activity measurement system, including a catheter configured to be inserted into a body part of a living subject and including a distal end including at least one electrode, signal processing circuitry coupled to the at least one electrode, and configured to receive an intracardiac electrogram (IEGM) signal from the at least one electrode and process the IEGM signal for output to a recording apparatus via a cable, which picks up surrounding electrical noise, and feedback circuitry configured to receive at least some of the electrical noise picked up by the cable, and provide a feedback signal indicative of the received electrical noise to the signal processing circuitry, which is configured to compensate at least partially for the electrical noise, which is not yet in the IEGM signal but will be added to the IEGM signal in the cable, responsively to the feedback signal to produce a noise-compensated IEGM signal for output to the recording apparatus via the cable.

Further in accordance with an embodiment of the present disclosure feedback circuitry includes a sensor configured to sense the at least some of the electrical noise picked up by the cable, the signal processing circuitry includes an analogue-to-digital convertor coupled to receive the IEGM signal from the at least one electrode as an input analogue IEGM signal, and configured to convert the input analogue IEGM signal to a digital IEGM signal, a digital signal filtering apparatus coupled to receive the digital IEGM signal and configured to filter noise from the received digital IEGM signal, a digital-to-analogue convertor coupled to receive the filtered digital IEGM signal, and configured to convert the filtered digital IEGM signal to a filtered analogue IEGM signal, and compensation circuitry coupled to receive the feedback signal and the filtered analogue IEGM signal, and configured to compensate at least partially for the electrical noise, which is not in the filtered analogue IEGM signal but will be added in the cable, responsively to the feedback signal to produce a noise-compensated analogue IEGM signal for output to the recording apparatus via the cable.

Still further in accordance with an embodiment of the present disclosure the sensor is an antenna or a coil.

Additionally, in accordance with an embodiment of the present disclosure the compensation circuitry is configured to generate a compensatory signal responsively to the feedback signal, and add the compensatory signal to the filtered analogue IEGM signal.

Moreover, in accordance with an embodiment of the present disclosure the compensatory circuitry is configured to generate the compensatory signal based on changing a phase of the feedback signal to be 180 degrees out-of-phase.

Further in accordance with an embodiment of the present disclosure the signal processing circuitry includes an analogue-to-digital convertor coupled to receive the IEGM signal from the at least one electrode as an input analogue IEGM signal, and configured to convert the input analogue IEGM signal to a digital IEGM signal, a digital signal filtering apparatus coupled to receive the digital IEGM signal and configured to filter noise from the received digital IEGM signal, compensation circuitry coupled to receive the filtered digital IEGM signal and the feedback signal, the feedback circuitry including an electrical connection running from the cable back to the compensation circuitry, the compensation circuitry being configured to compensate at least partially for the electrical noise, which is not in the digital IEGM signal but will be added in the cable, responsively to the feedback signal to produce a noise-compensated digital IEGM signal, and a digital-to-analogue convertor coupled to receive the noise-compensated digital IEGM signal, and configured to convert the noise-compensated digital IEGM signal to a noise-compensated analogue IEGM signal for output to the recording apparatus via the cable.

Still further in accordance with an embodiment of the present disclosure the compensation circuitry is configured to generate a compensatory signal responsively to the feedback signal, and add the compensatory signal to the filtered digital IEGM signal.

Additionally, in accordance with an embodiment of the present disclosure the compensation circuitry is configured to transform time windows of the feedback signal to a frequency domain, analyze the transformed time windows for presence of at least one frequency associated with the electrical noise, and generate the compensatory signal responsively to one transformed time window of the transformed time windows which has presence of the at least one frequency associated with the electrical noise.

Moreover, in accordance with an embodiment of the present disclosure the compensatory circuitry is configured to transform the one transformed time window to a time-domain signal, and generate the compensatory signal based on changing a phase of the time-domain signal to be 180 degrees out-of-phase.

There is also provided in accordance with another embodiment of the present disclosure, an electrical activity measurement method, including receiving an intracardiac electrogram (IEGM) signal from the at least one electrode of a catheter configured to be inserted into a body part of a living subject, processing the IEGM signal for output to a recording apparatus via a cable, which picks up surrounding electrical noise, receiving at least some of the electrical noise picked up by the cable, providing a feedback signal indicative of the received electrical noise, and compensating at least partially for the electrical noise, which is not yet in the IEGM signal but will be added to the IEGM signal in the cable, responsively to the feedback signal to produce a noise-compensated IEGM signal for output to the recording apparatus via the cable.

Further in accordance with an embodiment of the present disclosure, the method includes sensing the at least some of the electrical noise picked up by the cable, receiving the IEGM signal from the at least one electrode as an input analogue IEGM signal, converting the input analogue IEGM signal to a digital IEGM signal, filtering noise from the digital IEGM signal, converting the filtered digital IEGM signal to a filtered analogue IEGM signal, and compensating at least partially for the electrical noise, which is not in the filtered analogue IEGM signal but will be added in the cable, responsively to the feedback signal to produce a noise-compensated analogue IEGM signal for output to the recording apparatus via the cable.

Still further in accordance with an embodiment of the present disclosure, the method includes generating a compensatory signal responsively to the feedback signal, and adding the compensatory signal to the filtered analogue IEGM signal.

Additionally, in accordance with an embodiment of the present disclosure the generating includes generating the compensatory signal based on changing a phase of the feedback signal to be 180 degrees out-of-phase.

Moreover, in accordance with an embodiment of the present disclosure, the method includes receiving the IEGM signal from the at least one electrode as an input analogue IEGM signal, converting the input analogue IEGM signal to a digital IEGM signal, filtering noise from the received digital IEGM signal, compensating at least partially for the electrical noise, which is not in the digital IEGM signal but will be added in the cable, responsively to the feedback signal to produce a noise-compensated digital IEGM signal, and converting the noise-compensated digital IEGM signal to a noise-compensated analogue IEGM signal for output to the recording apparatus via the cable.

Further in accordance with an embodiment of the present disclosure, the method includes generating a compensatory signal responsively to the feedback signal, and adding the compensatory signal to the filtered digital IEGM signal.

Still further in accordance with an embodiment of the present disclosure, the method includes transforming time windows of the feedback signal to a frequency domain, analyzing the transformed time windows for presence of at least one frequency associated with the electrical noise, and wherein the generating includes generating the compensatory signal responsively to one transformed time window of the transformed time windows which has presence of the at least one frequency associated with the electrical noise.

Additionally, in accordance with an embodiment of the present disclosure, the method includes transforming the one transformed time window to a time-domain signal, wherein the generating includes generating the compensatory signal based on changing a phase of the time-domain signal to be 180 degrees out-of-phase.

BRIEF DESCRIPTION OF THE DRAWINGS

The present invention will be understood from the following detailed description, taken in conjunction with the drawings in which.

DESCRIPTION OF EXAMPLE EMBODIMENTS

Overview

Figure 1:
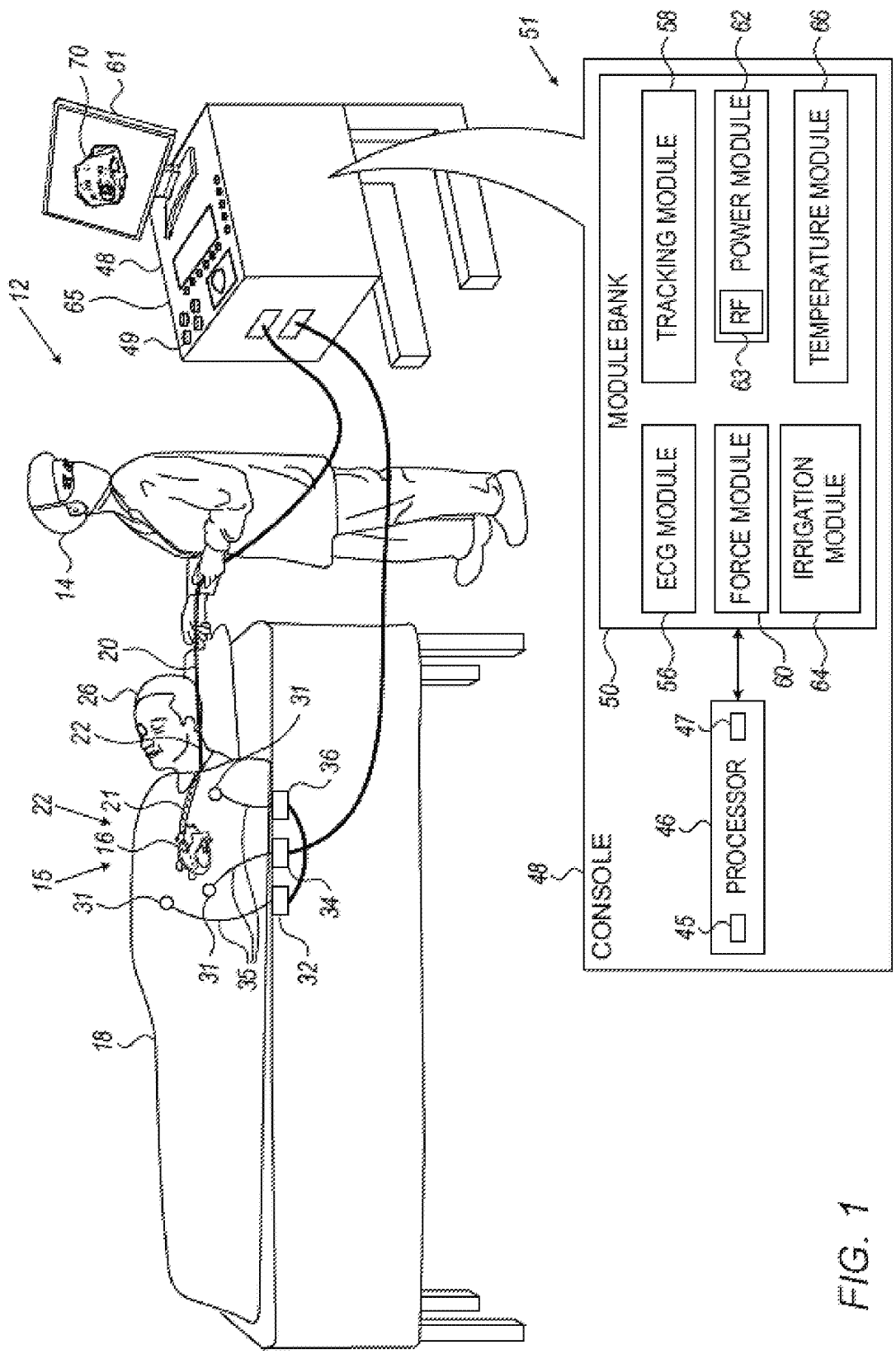
FIG. 1 is a partly pictorial, partly block diagram view of an electrical activity measurement apparatus constructed and operative in accordance with an embodiment of the present invention.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g. "about 90%" may refer to the range of values from 71% to 99%. In addition, as used herein, the terms "patient," "host," "user," and "subject" refer to any human or animal subject and are not intended to limit the systems or methods to human use, although use of the subject invention in a human patient represents a preferred embodiment.

As mentioned previously, during a cardiac electrophysiological (EP) investigative or ablation procedure, the leads between a patient and the electrical system used for the procedure, such as the Carto® system (Biosense Webster, Inc., of Irvine Calif.) and/or an external recording system, may pick up noise. Even where the noise is from known equipment, it may be difficult or even impossible to remove the equipment. For example, the Carto system may use an external uninterruptible power supply (UPS) which cannot be removed, but which generates electrical noise. The Carto system typically uses filtering techniques to clean the signal of the noise. However, the signal recorded by the external recording system may be very noisy, which may be a significant problem due to the very small voltages associated with electrophysiological signals.

Embodiments of the present invention reduce the problems associated with electrical noise pick-up in a cable between a catheter and the recording system by routing the intracardiac electrogram (IEGM) signal(s) captured by the catheter via signal processing circuitry (for example, which is part of the Carto system), which compensates for expected noise pickup prior to outputting the IEGM signal(s) to the external recording system.

The catheter is connected via a first cable to the signal processing circuitry and then with a second cable from the signal processing circuitry to the external recording system. The signal processing circuitry generally receives the IEGM signal via the first cable as an analogue signal which is then converted to a digital signal by the signal processing circuitry. At this stage, the signal processing circuitry may filter noise picked up in the first cable from the digital signal using any suitable digital filtering technique(s). The digital filtering may focus on removing signal components associated with electrical noise generated by surrounding electrical equipment which is typically based on a frequency of around 50 Hertz and possibly harmonic frequencies of 100 and 150 Hertz etc. At a later stage, the digital signal is converted back to an analogue signal by the signal processing circuitry for output to the external recording system via the second cable.

Electrical noise may also be picked up in the second cable. The external recording system is commonly an analogue device without noise filtering capabilities and therefore cannot filter the noise from the received IEGM signal via the second cable. The signal processing circuitry therefore compensates for this expected noise, which is not yet in the IEGM signal (while the IEGM signal is in the signal processing circuitry) but will be added to the IEGM signal in the second cable. In some embodiments, a sensor disposed near to the second cable senses at least some of the electrical noise picked up by the second cable and provides a feedback signal indicative of the sensed electrical noise to the signal processing circuitry. In other embodiments, an electrical connection feedbacks the signal in the cable to the signal processing circuitry. In both embodiments, the signal processing circuitry compensates at least partially for the electrical noise, which is not yet in the IEGM signal but will be added to the IEGM signal in the second cable, responsively to the feedback signal, to produce a noise-compensated IEGM signal for output to the recording apparatus via the second cable.

In some embodiments, the compensation for the expected noise is performed while the IEGM signal is in an analogue format.

System Description

Documents incorporated by reference herein are to be considered an integral part of the application except that, to the extent that any terms are defined in these incorporated documents in a manner that conflicts with definitions made explicitly or implicitly in the present specification, only the definitions in the present specification should be considered.

Figure 2:
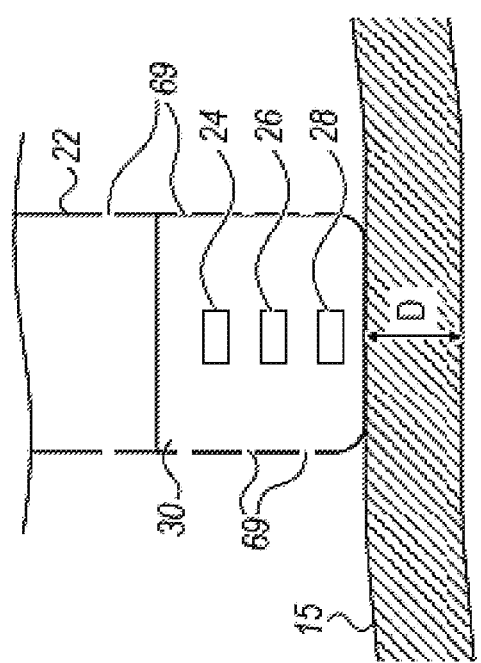
FIG. 2 is a schematic view of a catheter for use in the apparatus of FIG. 1.

Reference is now made to FIGS. 1 and 2. FIG. 1 is a partly pictorial, partly block diagram view of an electrical activity measurement apparatus 12 constructed and operative in accordance with an embodiment of the present invention. FIG. 2 is a schematic view of a catheter 20 for use in the apparatus 12 of FIG. 1. The catheter 20 has a distal end 22 and is configured to be inserted into a body part (e.g., heart) of a living subject. The procedure is performed by a physician 14, and in the description hereinbelow, the procedure is assumed to comprise a mapping procedure and/or an ablation of a portion of tissue 15 of a myocardium 16 of the heart of a human patient 18.

In order to perform the procedure, the physician 14 inserts the catheter 20 into a sheath 21 that has been pre-positioned in a lumen of the patient 18 so that the catheter 20 is inserted into a chamber of the heart. The sheath 21 is positioned so that the distal end 22 of the catheter 20 enters the heart of the patient 18. The distal end 22 comprises a position sensor 24 that enables the location and orientation of the distal end 22 to be tracked, a force sensor 26 that measures the force applied by the distal end 22 when it contacts the myocardium 16, and one or more temperature sensors 28 that measure the temperature at respective locations of the distal end 22. The distal end 22 also comprises one or more electrodes 30 which are used to apply radiofrequency power to the myocardium 16 in the chamber so as to ablate the myocardium 16. The electrode(s) 30 may also be used to acquire electro potentials from the myocardium 16.

The apparatus 12 is controlled by a system processor 46, which is located in an operating console 48 of the apparatus. The operating console 48 comprises controls of at least one user input device 49 which are used by the physician 14 to communicate with the processor 46. The software for processor 46 may be downloaded to the processor 46 in electronic form, over a network, for example. Alternatively, or additionally, the software may be provided on non-transitory tangible media, such as optical, magnetic, or electronic storage media.

The processor 46 may comprise a digital signal filtering apparatus 45, typically configured as a field programmable gate array (FPGA), and an analog-to-digital (A/D) converter integrated circuit 47. The processor 46 can pass the signal from the A/D convertor 47 to another processor and/or can be programmed to perform at least one algorithm disclosed herein, the algorithm comprising steps described hereinbelow. The processor 46 uses the digital signal filtering apparatus 45 and the A/D convertor 47, as well as features of modules which are described in more detail below, in order to perform the algorithm.

In order to operate the apparatus 12, the algorithm of the processor 46 communicates with a module bank 50, which has a number of modules used by the processor 46 to operate the apparatus 12. Thus, the module bank 50 comprises an electrocardiograph (ECG) module 56 coupled to receive signals from body surface electrodes 31 and/or electrodes 30, in order to provide the ECG signals to the processor 46. The body surface electrodes 31 and/or the electrode(s) 30 are configured for application to a body of a subject (e.g., the patient 18) and configured to output signals in response to electrical activity of a heart of the subject. The electrode(s) 30 is applied to the heart of the body via the catheter 20. The module bank 50 also includes a tracking module 58 which receives and analyzes signals from the position sensor 24, and which uses the signal analysis to generate a location and an orientation of the distal end 22. In some embodiments the position sensor 24 comprises one or more coils which provide the sensor signals in response to magnetic fields traversing the coils. In these embodiments, in addition to receiving and analyzing signals from sensor 24, tracking module 58 also controls radiators 32, 34, and 36 which radiate the magnetic fields traversing the position sensor 24. The radiators 32, 34, 36 are positioned in proximity to the myocardium 16, and are configured to radiate alternating magnetic fields into a region in proximity to the myocardium 16. A plurality of wire connections 35 link the operating console 48 with body the surface electrodes 31 and other components (such as the radiators 32, 34, 36 and the sensor 24) to enable the tracking module 58 to measure location and orientation coordinates of the catheter 20. In some embodiments, the tracking module 58 is configured to compute a relative location and a relative orientation of the catheter 20 with respect to the heart. Magnetic location and orientation tracking is described in U.S. Pat. Nos. 7,756,576 and 7,536,218, which are hereby incorporated by reference. The Carto system produced by Biosense Webster, of 33 Technology Drive, Irvine, Calif. 92618 USA, uses such a magnetic tracking system. The tracking module 58 is not limited to using magnetic based location and orientation tracking. Any suitable location and orientation tracking can be used, such as impedance-based or image-based tracking.

The apparatus 12 may receive image data from an external imaging modality, such as an MRI unit, CT unit or the like and includes image processors that can be incorporated in or invoked by the processor 46 for generating and displaying images. The image data may be registered with the tracking module 58 and a user interface screen 70 combining the received data and positions of the catheter 20 may be displayed to the physician 14 on a display 61. For example, the track of the distal end 22 of the catheter 20 may be shown on a three-dimensional (3D) representation of the heart of patient 18 that is displayed on the display 61. In some embodiments, the 3D representation of the heart may be at least partially computed based on mapping performed by the catheter 20.

The electrode(s) 30 and the body surface electrodes 31 may be used to measure tissue impedance at the ablation site as taught in U.S. Pat. No. 7,536,218, issued to Govari et al., which is herein incorporated by reference.

The module bank 50 also comprises a force module 60, a power module 62, an irrigation module 64, and a temperature module 66. The functions of these modules are explained below. The modules in the module bank 50, and the processor 46, are herein termed processing circuitry 51.

The force module 60 receives signals from the force sensor 26, and from the signals generates a magnitude of the contact force, herein assumed to be measured in grams, exerted by the distal end 22 on the tissue 15. In some embodiments the force sensor 26 is configured so that the signals it provides to the force module 60 enable the force module 60 to evaluate a direction of the force exerted by the distal end 22 on the tissue 15.

The power module 62 comprises a radiofrequency (RF) signal generator 63 which generates the radiofrequency power to be applied by the electrode(s) 30 to ablate the tissue 15 of the myocardium 16. The processor 46 and the power module 62 are able to adjust a power level, herein assumed to be measured in Watts, delivered by the electrode(s) 30, as well as a length of time, measured in seconds, during which the power is delivered.

The irrigation module 64 controls a rate of flow, herein assumed to be measured in mL/min, of irrigation fluid, typically normal saline solution, supplied to the distal end 22 by a pump 65 disposed in the operating console 48. The catheter 20 includes an irrigation channel through which to irrigate the myocardium 16. The irrigation fluid is expelled from irrigation holes 69 in the distal end 22. The pump 65 is configured to selectively pump the irrigation fluid into the irrigation channel at an idle rate and at one or more one non-idle rates (higher than the idle rate) according to a status of the ablation procedure.

The temperature module 66 receives a temperature signal provided by the temperature sensor 28 (or by each temperature sensor 28). The temperature signal is indicative of a temperature of the myocardium at a plurality of different times. The temperature module 66 determines the temperatures registered by each of the sensors 28. Typically, in the case of multiple sensors 28 the temperature module 66 determines a mean temperature of the distal end 22. Additionally, in the case of multiple sensors, the temperature module 66 may produce a map of the temperature distribution of the distal end 22.

In some embodiments, the catheter 20 may include any suitable catheter, for example, but not limited to, a focal catheter, a flower catheter with several deflectable arms, a balloon catheter, a lasso catheter or a basket catheter. The catheter may include electrode(s) 30 to acquire electro potentials, but may exclude or include one or more of the following: force sensor(s); temperature sensor(s); and irrigation channel(s).

Figure 3:
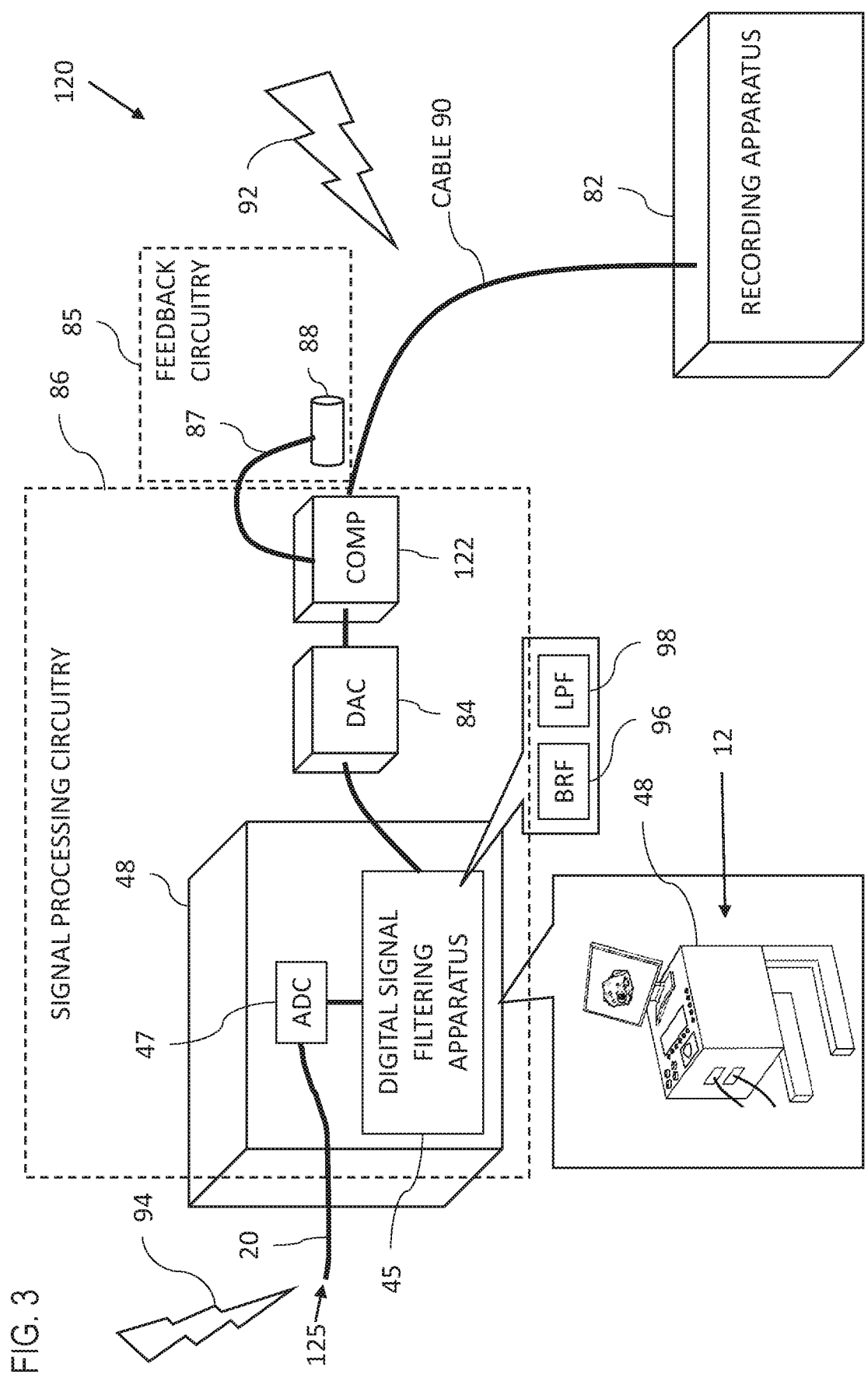
FIG. 3 is a schematic view of an electrical activity measurement system connected to a recording apparatus in accordance with an embodiment of the present invention.
Figure 4:
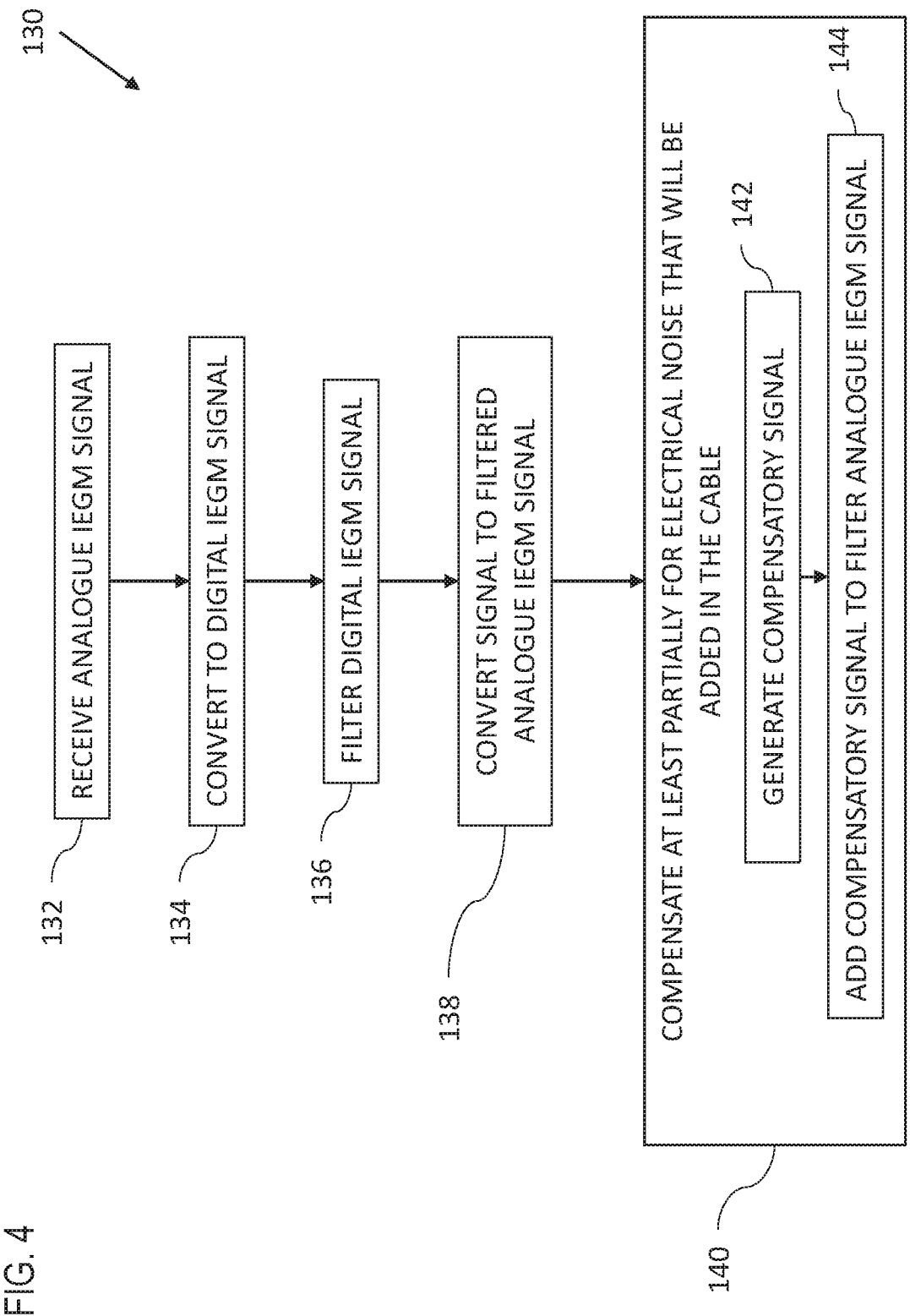
FIG. 4 is a flowchart including steps in a method of operation of the system of FIG. 3.

Reference is now made to FIGS. 3 and 4. FIG. 3 is a schematic view of an electrical activity measurement system 120 connected to the recording apparatus 82 in accordance with an embodiment of the present invention. FIG. 4 is a flowchart 130 including steps in a method of operation of the system 120 of FIG. 3.

The electrical activity measurement system 120 includes the apparatus 12 of FIG. 1, which includes the digital signal filtering apparatus 45 and the A/D convertor 47 disposed in the operating console 48. The electrical activity measurement system 120 also includes a compensation circuitry 122, and a digital-to-analogue (D/A) convertor 84. The digital signal filtering apparatus 45, the A/D convertor 47, the compensation circuitry 122, and the D/A convertor 84 are collectively described herein as signal processing circuitry 86. The electrical activity measurement system 120 also includes feedback circuitry 85, which comprises a sensor 88 and a cable 87, which electrically connects the sensor 88 with the compensation circuitry 122. The sensor 88 may comprise an antenna or coil, by way of example only. The sensor 88 provides a feedback signal to analogue compensation circuitry 122.

The signal processing circuitry 86 is coupled to the electrode(s) 30 (FIG. 2) of the catheter 20 (FIG. 2), and is configured to receive an intracardiac electrogram (IEGM) signal (or signals) 125 from the electrode(s) 30 (FIG. 2) and process the IEGM signal(s) 125 for output to the recording apparatus 82 via a cable 90, which picks up surrounding electrical noise 92. The catheter 20 may also pick up surrounding electrical noise 94 which may be identified and filtered by the digital signal filtering apparatus 45 as described in more detail below.

The sensor 88 of the feedback circuitry 85 is configured to sense, and thereby receive, at least some of the electrical noise 92 picked up by the cable 90 and provide a feedback signal indicative of the sensed (and received) electrical noise to the compensation circuitry 122. The compensation circuitry 122 is configured to compensate at least partially for the electrical noise 92, which is not yet in the IEGM signal(s) but will be added to the IEGM signal(s) in the cable 90, responsively to the feedback signal, to produce a noise-compensated IEGM signal for output to the recording apparatus 82 via the cable 90.

Compensation for the electrical noise 92 may be performed by adding a compensatory signal, having the same frequencies and amplitudes as the feedback signal, and generated to interfere with the electrical noise so as to cancel out the electrical noise added to the IEGM signal(s) in the cable 90. The compensatory signal may be based on changing the phase of the feedback signal to be 180 degrees out-of-phase. The electrical activity measurement system 120 is now described in more detail.

The A/D convertor 47 is coupled to receive (block 132) the IEGM signal(s) 125 from the electrode(s) 30 (FIG. 2) as an input analogue IEGM signal(s), and is configured to convert (block 134) the input analogue IEGM signal(s) to a digital IEGM signal(s).

The digital signal filtering apparatus 45 is coupled to receive the digital IEGM signal(s) and is configured to filter noise (block 136) from the received digital IEGM signal(s). The digital signal filtering apparatus 45 may include various filtering circuits, for example, but not limited to, a low pass filter 96 to remove signals with frequencies higher than a threshold frequency (for example 60 Hertz or 100 Hertz), and/or a band-rejection filter 98 to remove signals with frequencies in a range of frequencies (for example, from 100-200 Hz). The IEGM signals may include similar frequencies to noise, for example, in the 50 Hz range and therefore simply filtering out 50 Hz components using a low pass or band-rejection filter may not yield acceptable results. Therefore, other filtering methods may also be applied to remove noise associated with outside sources without adversely affecting the IEGM signals. Such methods are described in more detail with reference to FIGS. 8-10. At least some of the functionality of the digital signal filtering apparatus 45 and/or the A/D convertor 47 may be performed by one or more computers or processors executing software. The software may be downloaded to the computer(s) or processor(s) in electronic form, over a network, for example. Alternatively, or additionally, the software may be provided on non-transitory tangible media, such as optical, magnetic, or electronic storage media.

The D/A convertor 84 is coupled to receive the filtered digital IEGM signal(s), and is configured to convert (block 138) the filtered digital IEGM signal(s) to a filtered analogue IEGM signal(s).

The compensation circuitry 122 is coupled to receive the feedback signal (from the sensor 88) and the filtered analogue IEGM signal(s) (from the D/A convertor 84). The compensation circuitry 122 is configured to compensate (block 140) at least partially for the electrical noise, which is not in the filtered analogue IEGM signal(s) but will be added in the cable 90, responsively to the feedback signal, to produce a noise-compensated analogue IEGM signal for output to the recording apparatus 82 via the cable 90.

In some embodiments, the compensation circuitry 122 may be configured to generate (block 142) a compensatory signal responsively to the feedback signal, the compensatory signal having the same frequencies and amplitudes as the feedback signal, and generated to interfere with the electrical noise so as to cancel out the electrical noise added to the IEGM signal(s) in the cable 90. In some embodiments, the compensation circuitry 122 is configured to generate the compensatory signal based on changing the phase of the feedback signal to be 180 degrees out-of-phase. The compensation circuitry 122 is configured to add (block 144) the compensatory signal to the filtered analogue IEGM signal(s) to yield the noise-compensated analogue IEGM signal for output to the recording apparatus 82 via the cable 90.

Figure 5:
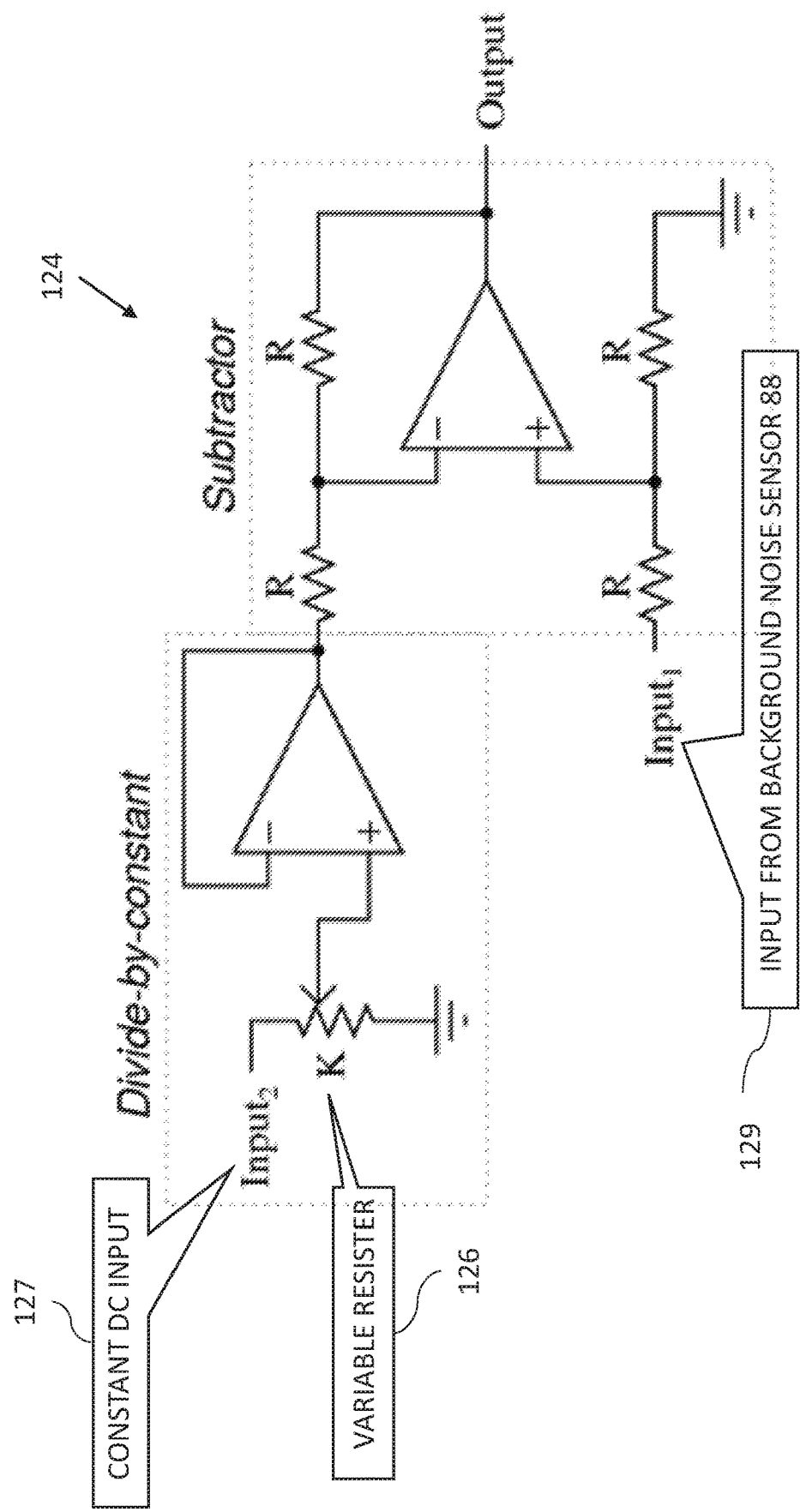
FIG. 5 is a view of a circuit comprised in compensation circuitry of the system of FIG. 3.

Reference is now made to FIG. 5, which is a view of a circuit 124 comprised in compensation circuitry 122 of the system 120 of FIG. 3.

The circuit 124 has two inputs ($input_1$ and $input_2$) and an output. $Input_1$ (block 129) takes the feedback signal from the sensor 88 as input. $Input_2$ is typically a constant DC voltage input (block 127). A gain control, is controlled by controlling a resistance K of a variable resistor 126. The variable resister may be controlled manually by a user who is viewing a signal on a monitor (not shown) of the recording apparatus 82 in order to minimize the noise shown included in the signal shown on the monitor. This adjustment typically is performed once at the beginning of the medical procedure. The output provides the compensatory signal which has an amplitude equal to $input_1$ minus ($input_2$/K). The variable resister can be set by a user looking at the signal received at the recording apparatus 82 via an oscilloscope and adjusting the gain until the noise is minimized.

Figure 6:
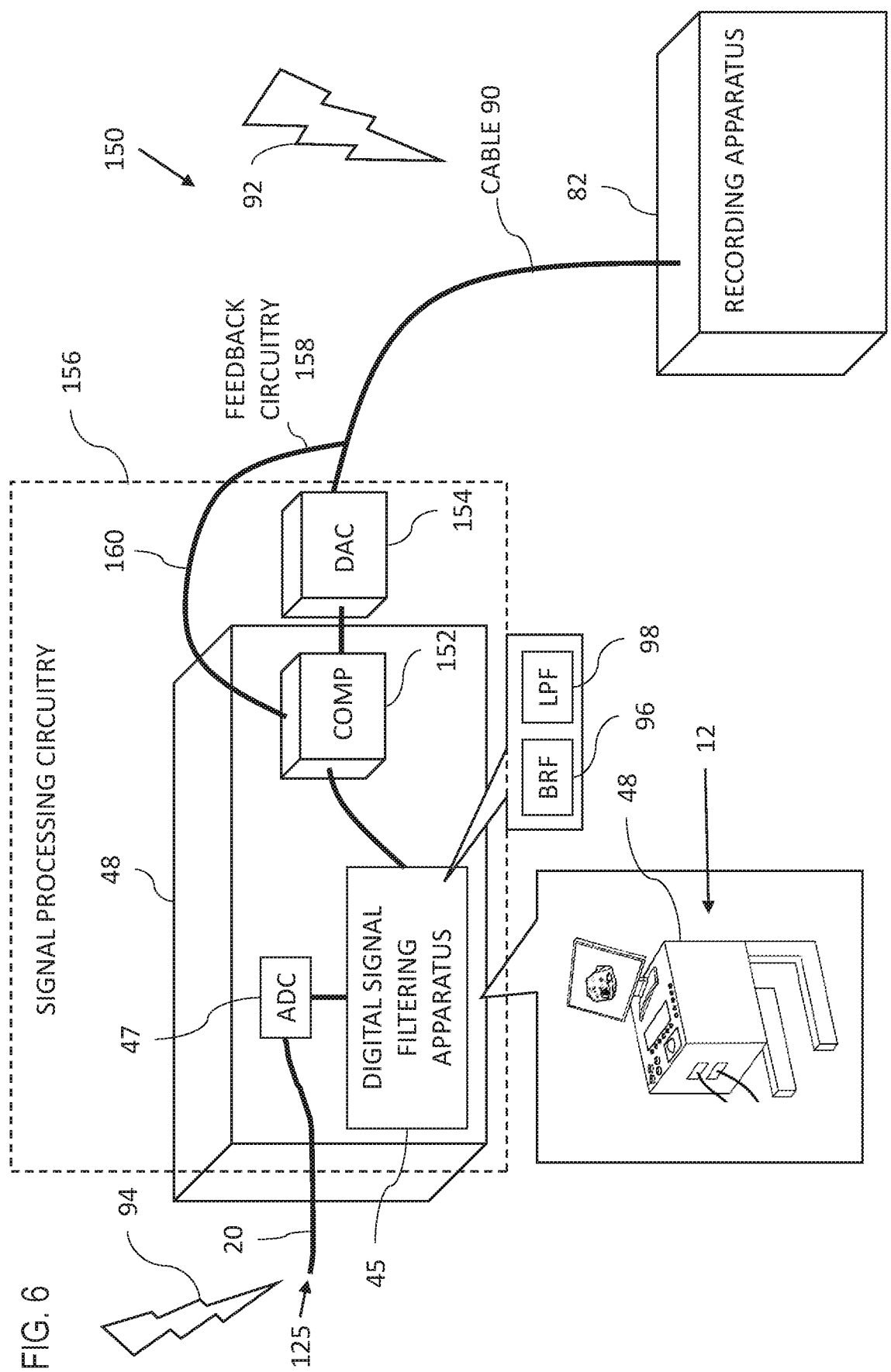
FIG. 6 is a schematic view of an electrical activity measurement system connected to a recording apparatus in accordance with an alternative embodiment of the present invention.
Figure 7:
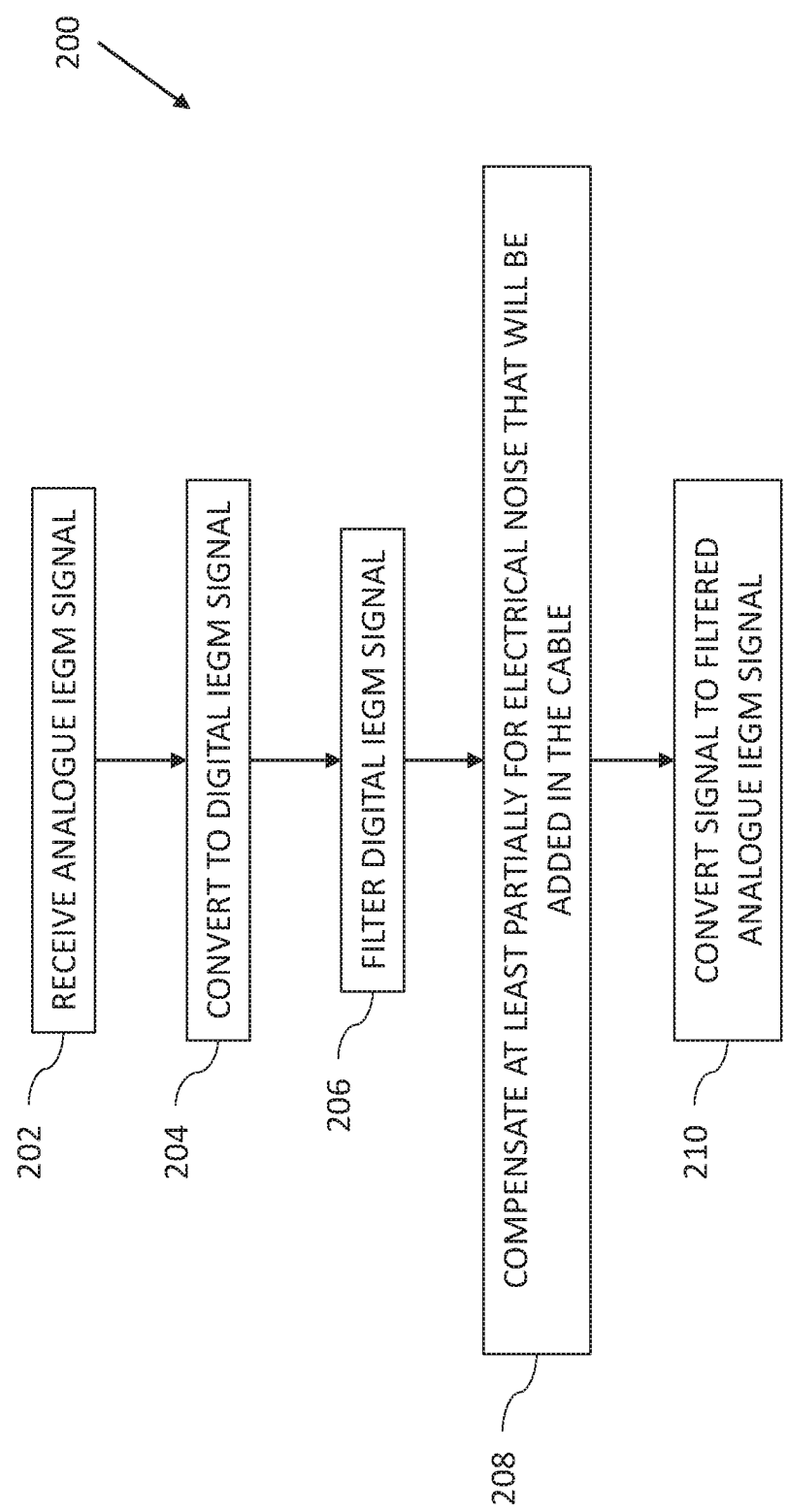
FIG. 7 is a flowchart including steps in a method of operation of the system of FIG. 6.

Reference is now made to FIGS. 6 and 7. FIG. 6 is a schematic view of an electrical activity measurement system 150 connected to the recording apparatus 82 in accordance with an alternative embodiment of the present invention. FIG. 7 is a flowchart 200 including steps in a method of operation of the system 150 of FIG. 6.

The electrical activity measurement system 150 includes the apparatus 12 of FIG. 1, which includes the digital signal filtering apparatus 45 and the A/D convertor 47 disposed in the operating console 48. The electrical activity measurement system 150 also includes compensation circuitry 152, and a digital-to-analogue (D/A) convertor 154. In some embodiments, the compensation circuitry 152 and/or the D/A convertor 154 may be disposed in the operating console 48. The digital signal filtering apparatus 45, the A/D convertor 47, the compensation circuitry 152, and the D/A convertor 154 are collectively described herein as signal processing circuitry 156. The electrical activity measurement system 150 also includes feedback circuitry 158, which comprises an electrical connection 160 running back from the cable 90 to the compensation circuitry 152. The cable 90 connects the D/A convertor 154 to the recording apparatus 82.

The signal processing circuitry 156 is coupled to the electrode(s) 30 (FIG. 2) of the catheter 20 (FIG. 2), and is configured to receive an intracardiac electrogram (IEGM) signal (or signals) 125 from the electrode(s) 30 (FIG. 2) and process the IEGM signal(s) 125 for output to the recording apparatus 82 via the cable 90, which picks up surrounding electrical noise 92. The catheter 20 may also pick up surrounding electrical noise 94 which may be identified and filtered by the digital signal filtering apparatus 45 as described in more detail below.

The electrical connection 160 of the feedback circuitry 85 is configured to receive, at least some of the electrical noise 92 picked up by the cable 90 and provide a feedback signal indicative of the received electrical noise to the compensation circuitry 152. The electrical connection 160 may be connected to any suitable point along the cable 90 as the electrical noise 92 is typically picked up by the signal along the length of the cable 90. The compensation circuitry 152 is configured to compensate at least partially for the electrical noise 92, which is not yet in the IEGM signal(s) but will be added to the IEGM signal(s) in the cable 90, responsively to the feedback signal, to produce a noise-compensated IEGM signal for output to the recording apparatus 82 via the cable 90.

Compensation for the electrical noise 92 may be performed by adding a compensatory signal, having the same frequencies and amplitudes as the noise in the feedback signal, and generated to interfere with the electrical noise so as to cancel out the electrical noise added to the IEGM signal(s) in the cable 90. Generation of the compensatory signal is described in more detail below with reference to FIGS. 8-10. The electrical activity measurement system 120 is now described in more detail.

The A/D convertor 47 is coupled to receive (block 202) the IEGM signal 125 from the electrode(s) 30 (FIG. 2) as an input analogue IEGM signal. The A/D convertor 47 is configured to convert (block 204) the input analogue IEGM signal to a digital IEGM signal.

The digital signal filtering apparatus 45 is coupled to receive the digital IEGM signal and configured to filter (block 206) noise from the received digital IEGM signal. The digital signal filtering apparatus 45 may include various filtering circuits, for example, but not limited to, the low pass filter 96 to remove signals with frequencies higher than a threshold frequency (for example 100 Hertz), and/or the band-rejection filter 98 to remove signals with frequencies in a range of frequencies (for example, from 100-200 Hz). The IEGM signals may include similar frequencies to noise, for example, in the 50 Hz range and therefore simply filtering out 50 Hz components using a low pass or band-rejection filter may not yield acceptable results. Therefore, other filtering methods may also be applied to remove noise associated with outside sources without adversely affecting the IEGM signals. Such methods are described in more detail with reference to FIGS. 8-10.

The compensation circuitry 152 is coupled to receive the filtered digital IEGM signal (from the digital signal filtering apparatus 45) and the feedback signal (via the electrical connection 160 from the cable 90). The compensation circuitry 152 is configured to compensate (block 208) at least partially for the electrical noise, which is not in the digital IEGM signal but will be added in the cable 90, responsively to the feedback signal to produce a noise-compensated digital IEGM signal. The step of block 208 is described in more detail with reference to FIGS. 8-10.

At least some of the functionality of the digital signal filtering apparatus 45 and/or the A/D convertor 47 and/or the compensation circuitry 152 may be performed by one or more computers (or processors) executing software. The software may be downloaded to the computer(s) or processor(s) in electronic form, over a network, for example. Alternatively, or additionally, the software may be provided on non-transitory tangible media, such as optical, magnetic, or electronic storage media.

The D/A convertor 154 is coupled to receive the noise-compensated digital IEGM signal from the compensation circuitry 152, and configured to convert (block 210) the noise-compensated digital IEGM signal to a noise-compensated analogue IEGM signal for output to the recording apparatus 82 via the cable 90.

Figure 8:
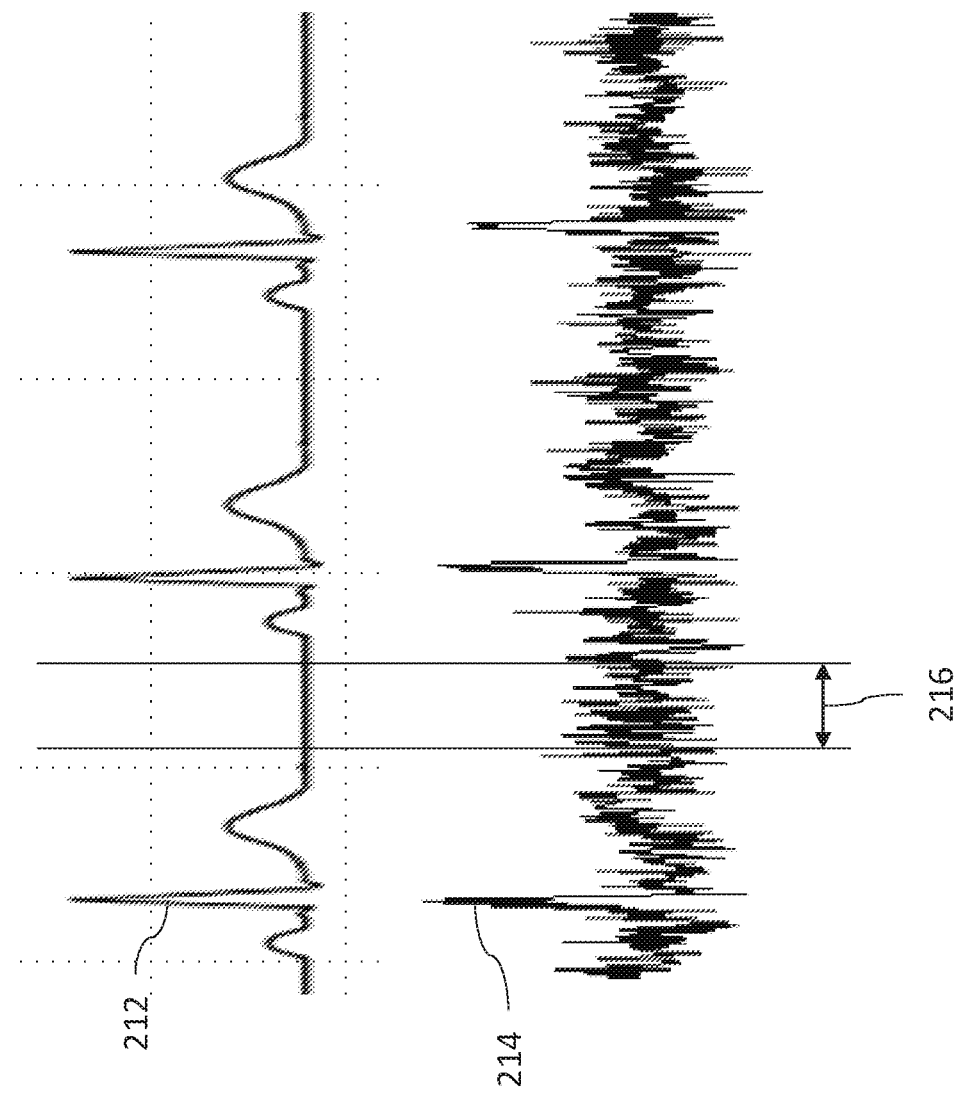
FIGS. 8 and 9 are views of electrical signals illustrating the method of FIG. 7.
Figure 9:
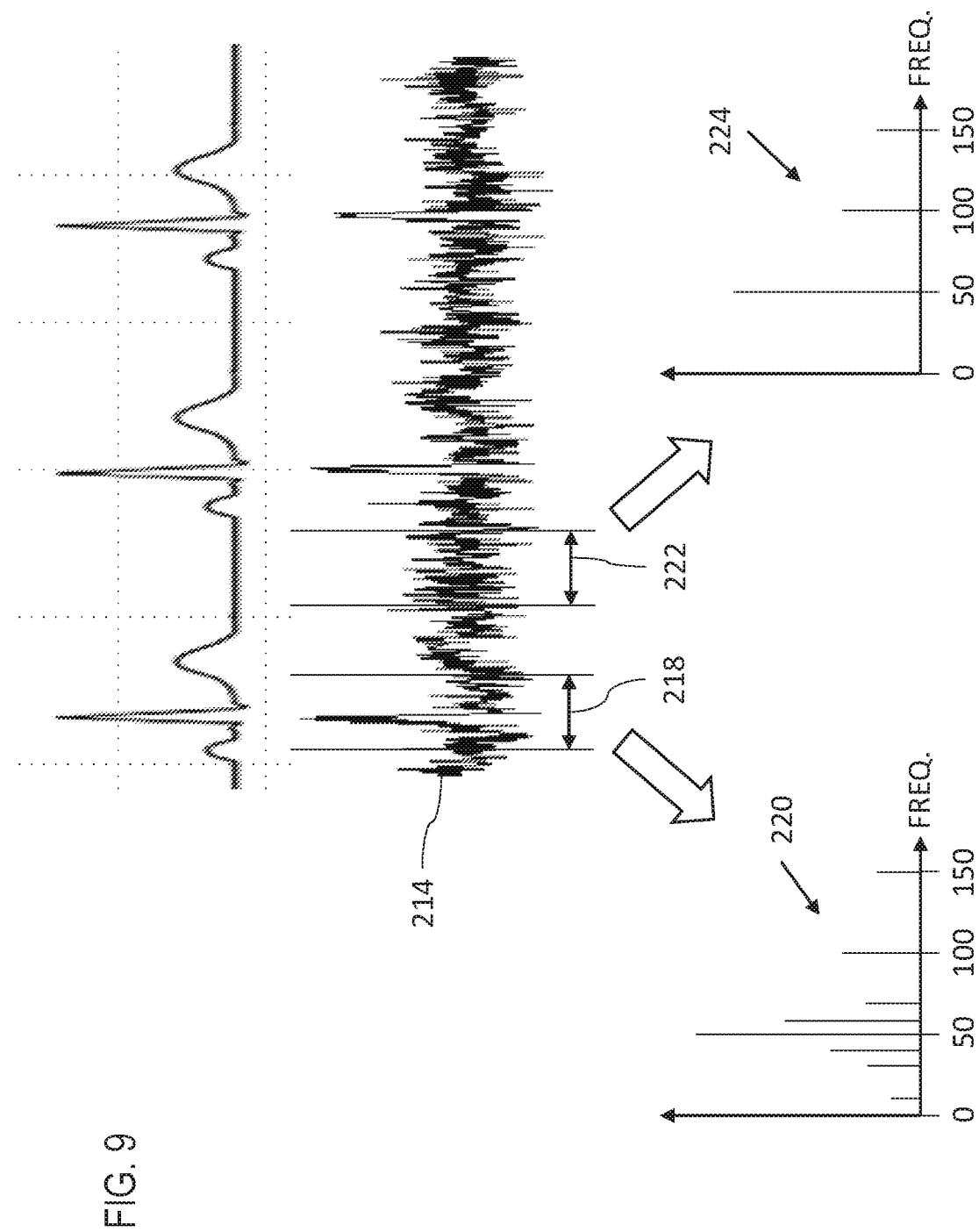

Reference is now made to FIGS. 8 and 9, which are views of electrical signals illustrating the method of FIG. 7. FIG. 8 shows a noise-free IEGM signal 212 and a noisy IEGM signal 214. The noise in the noisy IEGM signal 214 may have any frequency or frequencies of noise. In some cases, the noisy IEGM signal 214 may include 50 Hz noise from surrounding electrical appliances, as well as harmonics, e.g., 100 Hz and 150 Hz, related to the noise from the surrounding electrical appliances. However, as the IEGM signal detected by the electrode(s) 30 (FIG. 2) may include similar frequencies to the noise, for example, in the 50 Hz range, simply filtering out 50 Hz components using a low pass or band-rejection filter may also destroy some of the IEGM signal as detected by the electrode(s) 30.

FIG. 8 shows that a time-window 216 of the noise-free IEGM signal 212 is flat and does not have any amplitude associated with the IEGM signal detected by the electrode(s) 30. In the same time-window 216, the noisy IEGM signal 214 includes noise, which may be assumed to correspond to the noise alone.

The above is further illustrated in FIG. 9 which shows two time-windows of the noisy IEGM signal 214 being selected. A part of the noisy IEGM signal 214 in a first time-window 218 is transformed using a suitable transform, such as a Discrete Fourier Transform (DFT) from the time-domain to the frequency domain. A result of the transform is shown in a graph 220, which shows that the part of the noisy IEGM signal 214 in the first time-window 218 includes components of 50 Hz, 100 Hz, 150 Hz as well as many other frequency components. It may therefore be concluded that the part of the noisy IEGM signal 214 in the first time-window 218 includes the noise as well as the IEGM signal detected by the electrode(s) 30 (FIG. 2).

A part of the noisy IEGM signal 214 in a second time-window 222 is transformed using any suitable transform, such as a Discrete Fourier Transform (DFT) from the time-domain to the frequency domain. A result of the transform is shown in a graph 224, which shows that the part of the noisy IEGM signal 214 in the second time-window 222 only includes frequency components of 50 Hz, 100 Hz, 150 Hz. It may therefore be concluded that the part of the noisy IEGM signal 214 in the second time-window 222 only includes the noise and not the IEGM signal detected by the electrode(s) 30 (FIG. 2). The part of the noisy IEGM signal 214 in the second time-window 222 may then be transformed back from the frequency-domain to the time-domain, using any suitable transform, for example, using an inverse DFT. The time-domain signal may then be used to generate a compensatory signal based on changing a phase of the time-domain signal to be 180 degrees out-of-phase.

The compensatory signal may then be added to the filtered digital IEGM signal, as described in more detail with reference to FIG. 10.

As the time-window, which does not include the IEGM signal detected by the electrode(s) 30 (FIG. 2), is generally not readily apparent from the noisy IEGM signal 214, different time-windows of the noisy IEGM signal 214 are analyzed, using the above method, to determine which time window does not include the IEGM signal detected by the electrode(s) 30. In some embodiments, as many time-windows of the noisy IEGM signal 214 may include some frequencies other than the noise (e.g., other than the 50 Hz component and its harmonies), the system may select a time-window, which includes some frequencies other than the noise if the magnitude of the frequencies other than the noise is below a given threshold, to form the basis of the compensatory signal.

Figure 10:
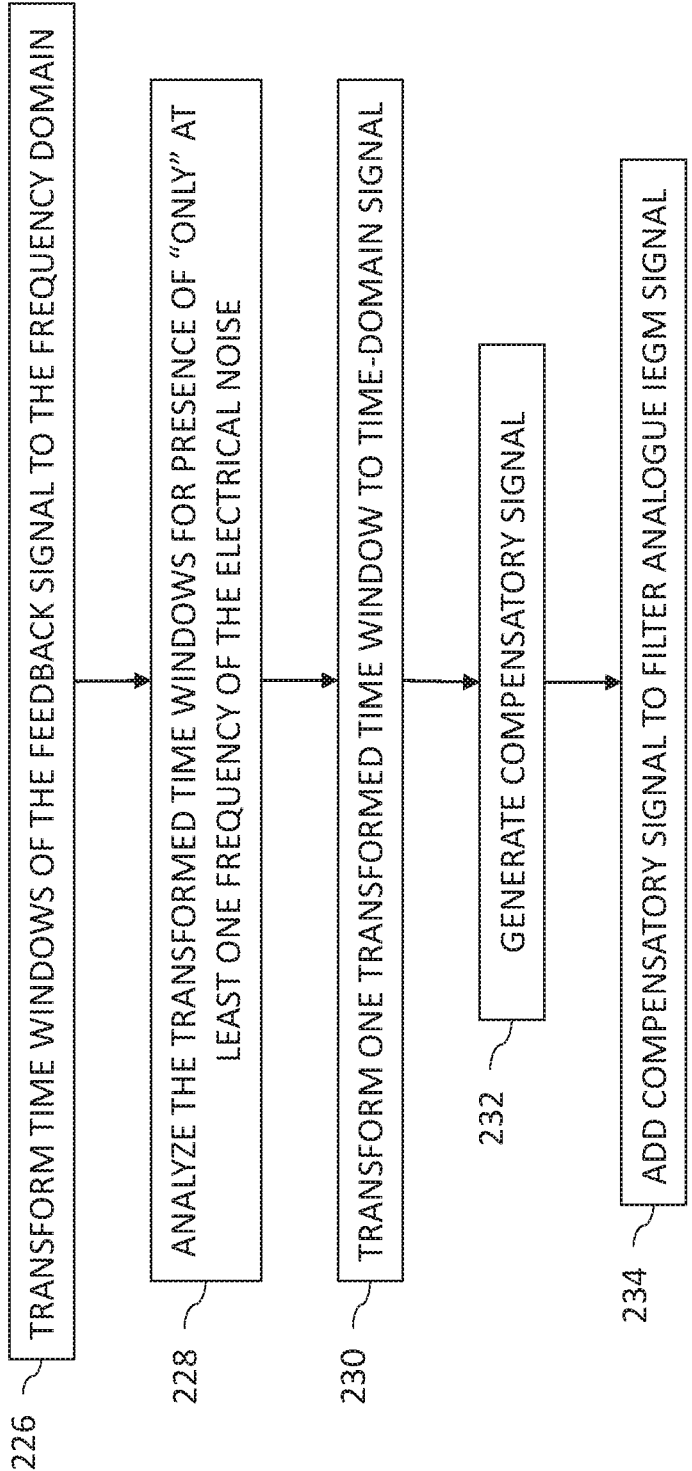
FIG. 10 is a flowchart including sub steps of one of the steps of the method of FIG. 7.

Reference is now made to FIG. 10, which is a flowchart including sub steps of the step of block 208 of the method of FIG. 7. The compensation circuitry 152 is configured to transform (block 226) time windows of the feedback signal to a frequency domain, for example, using a DFT. The step between time-windows as well as the size of the time-windows may be set to any suitable value. In some embodiments, the step between time windows may be in the range of 0.1 to 0.4 seconds and the size of the time windows may be in the range of 0.1 to 0.5 seconds, by way of example only.

The compensation circuitry 152 is configured to analyze (block 228) the transformed time windows of the feedback signal for presence of at least one frequency associated with the electrical noise without frequencies associated with the IEGM signal as detected by the electrode(s) 30 (FIG. 2) or with frequencies associated with the IEGM signal as detected by the electrode(s) 30 but below a given threshold magnitude. The compensation circuitry 152 selects one of the transformed time windows without frequencies associated with the IEGM signal as detected by the electrode(s) 30 (FIG. 2) or with frequencies associated with the IEGM signal as detected by the electrode(s) 30 but below a given threshold magnitude. The compensation circuitry 152 is configured to transform (block 230) the selected transformed time window of the feedback signal to a time-domain signal, for example, using an inverse DFT.

The compensation circuitry 152 is configured to generate (block 232) the compensatory signal responsively to the time-domain signal, which is based on transforming the selected transformed time window (of the feedback signal), which has presence of the at least one frequency associated with the electrical noise, of the feedback signal (without other frequencies or with other frequencies but below a given threshold). In some embodiments, the compensation circuitry 152 is configured to generate the compensatory signal based on changing a phase of the time-domain signal to be 180 degrees out-of-phase. The compensation circuitry 152 is configured to add (block 234) the compensatory signal to the filtered digital IEGM signal.

As the feedback signal may be continuously changing, the compensatory signal may be repeatedly generated from the feedback signal, for example, but not limited to, every one or two seconds.

Reference is again made to FIGS. 3 and 5. It was previously mentioned that the electrical activity measurement system 120 uses the circuit 124 as part of the compensation circuitry 122, and the gain control of the circuit 124 may be controlled by manually controlling the resistance K of the variable resistor 126. In other embodiments, the gain control of the circuit 124 may be controlled automatically by the digital signal filtering apparatus 45 using a signal from the digital signal filtering apparatus 45 to adjust the variable resistor 126. The digital signal filtering apparatus 45 may compute the gain control for setting the variable resistor 126 as follows. The gain control is a ratio of the electrical noise 92 included in the signal in the cable 90 to the electrical noise 92 sensed by the sensor 88. The electrical noise 92 included in the signal in the cable 90 may be determined by taking an electrical connection back from the cable 90 to the digital signal filtering apparatus 45 where the signal is measured in the "flat region" of the IEGM signal, e.g., the time-window 216 (FIG. 8). The "flat region" may be determined using the method described above with reference to FIGS. 8 and 9 by taking various time-windows of the signal and analyzing the frequency components of the time windows until the "flat region" is identified. The electrical noise 92 sensed by the sensor 88 may be determined by taking an electrical connection from the sensor 88 to the digital signal filtering apparatus 45, which measures the level of noise in the signal received from the sensor 88. The computation of the gain ratio and the setting of the variable resistor 126 may be performed at the start of a medical procedure or at any suitable time.

Various features of the invention which are, for clarity, described in the contexts of separate embodiments may also be provided in combination in a single embodiment. Conversely, various features of the invention which are, for brevity, described in the context of a single embodiment may also be provided separately or in any suitable sub-combination.

The embodiments described above are cited by way of example, and the present invention is not limited by what has been particularly shown and described hereinabove. Rather the scope of the invention includes both combinations and subcombinations of the various features described hereinabove, as well as variations and modifications thereof which would occur to persons skilled in the art upon reading the foregoing description and which are not disclosed in the prior art.

What is claimed is:

1. An electrical activity measurement system, comprising:
a catheter configured to be inserted into a body part of a living subject and including a distal end comprising at least one electrode;
signal processing circuitry coupled to the at least one electrode, and configured to receive an intracardiac electrogram (IEGM) signal from the at least one electrode and process the IEGM signal for output to a recording apparatus via a cable, which picks up surrounding electrical noise; and
feedback circuitry configured to: receive at least some of the electrical noise picked up by the cable; and provide a feedback signal indicative of the received electrical noise to the signal processing circuitry, which is configured to compensate at least partially for the electrical noise, which is not yet in the IEGM signal but will be added to the IEGM signal in the cable, responsively to the feedback signal to produce a noise-compensated IEGM signal for output to the recording apparatus via the cable.

2. The system according to claim 1, wherein:
the feedback circuitry includes a sensor configured to sense at least some of the electrical noise picked up by the cable; and
the signal processing circuitry comprises:

an analogue-to-digital convertor coupled to receive the IEGM signal from the at least one electrode as an input analogue IEGM signal, and configured to convert the input analogue IEGM signal to a digital IEGM signal;

a digital signal filtering apparatus coupled to receive the digital IEGM signal and configured to filter noise from the received digital IEGM signal;

a digital-to-analogue convertor coupled to receive the filtered digital IEGM signal, and configured to convert the filtered digital IEGM signal to a filtered analogue IEGM signal; and compensation circuitry coupled to receive the feedback signal and the filtered analogue IEGM signal, and configured to compensate at least partially for the electrical noise, which is not in the filtered analogue IEGM signal but will be added in the cable, responsively to the feedback signal to produce a noise-compensated analogue IEGM signal for output to the recording apparatus via the cable.

3. The system according to claim 2, wherein the sensor comprises an antenna or a coil.

4. The system according to claim 2, wherein the compensation circuitry is configured to: generate a compensatory signal responsively to the feedback signal; and add the compensatory signal to the filtered analogue IEGM signal.

5. The system according to claim 4, wherein the compensatory circuitry is configured to generate the compensatory signal based on changing a phase of the feedback signal to be approximately 180 degrees out-of-phase.

6. The system according to claim 1, wherein the signal processing circuitry comprises:

an analogue-to-digital convertor coupled to receive the IEGM signal from the at least one electrode as an input analogue IEGM signal, and configured to convert the input analogue IEGM signal to a digital IEGM signal;

a digital signal filtering apparatus coupled to receive the digital IEGM signal and configured to filter noise from the received digital IEGM signal;

compensation circuitry coupled to receive the filtered digital IEGM signal and the feedback signal, the feedback circuitry comprising an electrical connection running from the cable back to the compensation circuitry, the compensation circuitry being configured to compensate at least partially for the electrical noise, which is not in the digital IEGM signal but will be added in the cable, responsively to the feedback signal to produce a noise-compensated digital IEGM signal; and a digital-to-analogue convertor coupled to receive the noise-compensated digital IEGM signal, and configured to convert the noise-compensated digital IEGM signal to a noise-compensated analogue IEGM signal for output to the recording apparatus via the cable.

7. The system according to claim 6, wherein the compensation circuitry is configured to: generate a compensatory signal responsively to the feedback signal; and add the compensatory signal to the filtered digital IEGM signal.

8. The system according to claim 7, wherein the compensation circuitry is configured to:

transform time windows of the feedback signal to a frequency domain;

analyze the transformed time windows for presence of at least one frequency associated with the electrical noise; and generate the compensatory signal responsively to one transformed time window of the transformed time windows which has presence of the at least one frequency associated with the electrical noise.

9. The system according to claim 8, wherein the compensatory circuitry is configured to:

transform the one transformed time window to a time-domain signal; and generate the compensatory signal based on changing a phase of the time-domain signal to be approximately 180 degrees out-of-phase.

10. An electrical activity measurement method, comprising:

receiving an intracardiac electrogram (IEGM) signal from the at least one electrode of a catheter configured to be inserted into a body part of a living subject;

processing the IEGM signal for output to a recording apparatus via a cable, which picks up surrounding electrical noise;

receiving at least some of the electrical noise picked up by the cable;

providing a feedback signal indicative of the received electrical noise; and compensating at least partially for the electrical noise, which is not yet in the IEGM signal but will be added to the IEGM signal in the cable, responsively to the feedback signal to produce a noise-compensated IEGM signal for output to the recording apparatus via the cable.

11. The method according to claim 10, further comprising:

sensing the at least some of the electrical noise picked up by the cable;

receiving the IEGM signal from the at least one electrode as an input analogue IEGM signal;

converting the input analogue IEGM signal to a digital IEGM signal;

filtering noise from the digital IEGM signal;

converting the filtered digital IEGM signal to a filtered analogue IEGM signal; and compensating at least partially for the electrical noise, which is not in the filtered analogue IEGM signal but will be added in the cable, responsively to the feedback signal to produce a noise-compensated analogue IEGM signal for output to the recording apparatus via the cable.

12. The method according to claim 11, further comprising: generating a compensatory signal responsively to the feedback signal; and adding the compensatory signal to the filtered analogue IEGM signal.

13. The method according to claim 12, wherein the generating includes generating the compensatory signal based on changing a phase of the feedback signal to be 180 degrees out-of-phase.

14. The method according to claim 10, further comprising:

receiving the IEGM signal from the at least one electrode as an input analogue IEGM signal;

converting the input analogue IEGM signal to a digital IEGM signal;

filtering noise from the received digital IEGM signal;

compensating at least partially for the electrical noise, which is not in the digital IEGM signal but will be added in the cable, responsively to the feedback signal to produce a noise-compensated digital IEGM signal; and converting the noise-compensated digital IEGM signal to a noise-compensated analogue IEGM signal for output to the recording apparatus via the cable.

15. The method according to claim 14, further comprising: generating a compensatory signal responsively to the feedback signal; and adding the compensatory signal to the filtered digital IEGM signal.

16. The method according to claim 15, further comprising:
- transforming time windows of the feedback signal to a frequency domain; and
- analyzing the transformed time windows for presence of at least one frequency associated with the electrical noise, and wherein the generating includes generating the compensatory signal responsively to one transformed time window of the transformed time windows which has presence of the at least one frequency associated with the electrical noise.

17. The method according to claim 16, further comprising transforming the one transformed time window to a time-domain signal, wherein the generating includes generating the compensatory signal based on changing a phase of the time-domain signal to be 180 degrees out-of-phase.

* * * * *